United States Patent [19]
Grethe et al.

[11] 3,953,453
[45] Apr. 27, 1976

[54] TRIFLUOROMETHYL SUBSTITUTED ANALOGS OF QUININE AND QUINIDINE

[75] Inventors: Guenter Grethe, North Caldwell; Milan Radoje Uskokovic, Upper Montclair, both of N.J.

[73] Assignee: Hoffmann-La Roche Inc., Nutley, N.J.

[22] Filed: Nov. 11, 1974

[21] Appl. No.: 522,677

Related U.S. Application Data

[63] Continuation-in-part of Ser. No. 422,645, Dec. 7, 1973, abandoned.

[52] U.S. Cl. ............................ 260/284; 260/283 R; 260/288 E; 424/259
[51] Int. Cl.² .................................... C07D 453/04
[58] Field of Search ................................... 260/284

[56] References Cited
UNITED STATES PATENTS

| | | |
|---|---|---|
| 3,663,552 | 5/1972 | Yardley et al. ................ 260/284 |
| 3,772,302 | 11/1973 | Gutzwiller et al. ............ 260/284 |
| 3,857,846 | 12/1974 | Gutzwiller et al. ............ 260/284 |

*Primary Examiner*—R. J. Gallagher
*Assistant Examiner*—Mary Vaughn
*Attorney, Agent, or Firm*—Samuel L. Welt; George M. Gould; William G. Isgro

[57] ABSTRACT

Trifluoromethyl substituted analogs of quinine and quinidine are prepared by reacting a 4-quinolyllithium compound with a 4,5-erythro-5-ethyl-(or vinyl)-quinuclidine-2 ξ-carboxaldehyde or the corresponding quinuclidine-2 ξ-carboxylic acid alkyl ester. The end products are useful as antimalarial agents.

21 Claims, No Drawings

TRIFLUOROMETHYL SUBSTITUTED ANALOGS OF QUININE AND QUINIDINE

CROSS-REFERENCE TO RELATED APPLICATIONS

This application is a continuation-in-part application of U.S. patent application Ser. No. 422,645, filed Dec. 7, 1973, now abandoned.

BRIEF SUMMARY OF THE INVENTION

The invention relates to the preparation of compounds of the formulas I and II

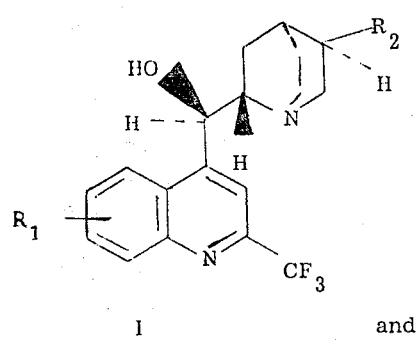

I and

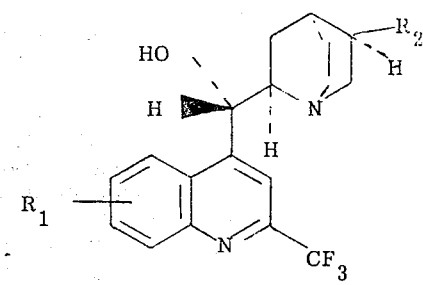

II enantiomers and racemates thereof;

wherein $R_1$ is halogen or trifluoromethyl; and $R_2$ is ethyl or vinyl and salts thereof with pharmaceutically acceptable acids.

DETAILED DESCRIPTION OF THE INVENTION

The term "halogen" denotes all the halogens, i.e., bromine, chlorine, fluorine and iodine; chlorine is preferred.

The compounds of formulas I and II are prepared as described hereinafter.

A mixture of epimeric 5(R)-ethyl-(or vinyl)-4(S)-quinuclidine-2ξ-carboxaldehydes of the formula

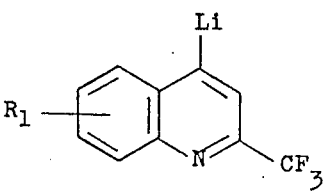

III wherein $R_2$ is as previously described, enantiomers or racemates thereof, is reacted with a 4-quinolyllithium compound of the formula

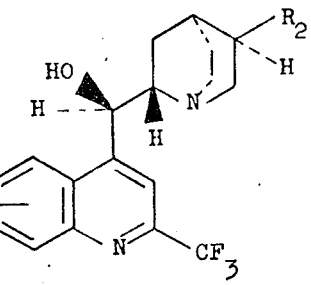

IV wherein $R_1$ is as previously described, to yield the corresponding α(R)-[5(R)-ethyl(or vinyl)-4(S)-quinuclidin-2(S)-yl]-4-quinolinemethanol of the formula

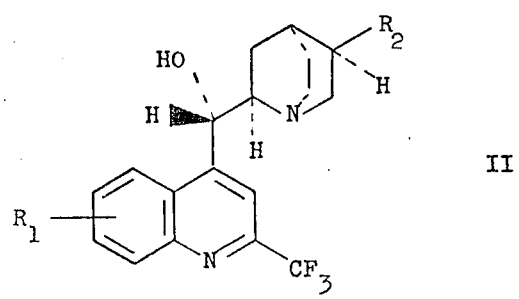

I wherein $R_1$ and $R_2$ are as previously described, enantiomer or racemate thereof, and α(S)-[5(R)-ethyl(or vinyl)-4(S)-quinuclidin-2(R)-yl]-4-quinolinemethanol of the formula

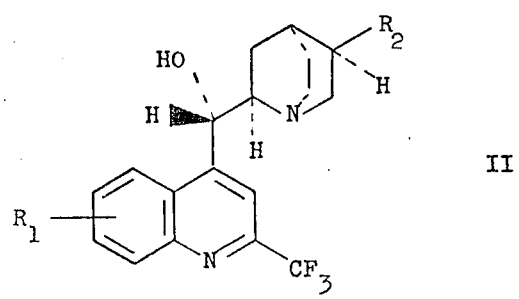

II wherein $R_1$ and $R_2$ are as previously described, enantiomer or racemate thereof. The 4-quinolyllithium compound of formula IV is reacted in equimolar or greater than equimolar proportions with the compound of formula III. The reaction is conveniently carried out at room temperature or below room temperature, preferably at a temperature in the range of between about 0° and about −70°, in the presence of an inert organic solvent, for example, an ether, such as diethylether, tetrahydrofuran, dioxane and diglyme; or a hydrocarbon, such as benzene, toluene and the like. The compounds of formulas I and II are then recovered from the reaction mixture utilizing conventional procedures, for example, crystallization and the like.

The compounds of formulas I and II can also be prepared by reacting a mixture of epimeric 5(R)-ethyl(or vinyl)-4(S)-quinuclidine-2ξ-carboxylic acid alkyl esters of the formula

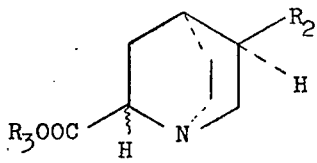  V wherein $R_2$ is as previously described and $R_3$ is lower alkyl, enantiomers or racemates, with a 4-quinolyllithium compound of the formula

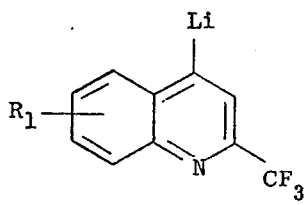  IV wherein $R_1$ is as previously described, to yield the corresponding mixture of epimeric 4-[5(R)-ethyl(or vinyl)-4(S)-quinuclidin-2ξ-ylcarbonyl]quinolines of the formula

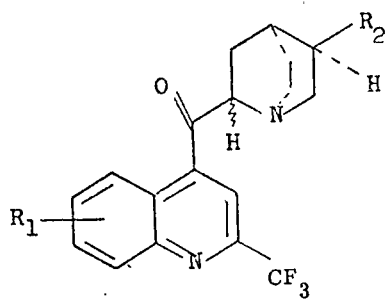  VI wherein $R_1$ and $R_2$ are as previously described, enantiomers or racemates thereof. The 4-quinolyllithium compound of formula IV is reacted in equimolar or greater than equimolar proportions with the compound of formula V. Preferably, two molar proportions of the quinolyllithium compound are utilized. The reaction is conveniently effected at room temperature or below room temperature, preferably in the range of about between 0° and about −70°C. Suitably, an inert solvent, for example, an ether, such as diethyl ether, tetrahydrofuran, dioxane and diglyme, or a hydrocarbon such as benzene, toluene, and the like, may be utilized. Further, the reaction may be conveniently carried out in the presence of complexing agents such as 1,4-diazabicyclo[2.2.2]octane or tetramethylethylenediamine.

The conversion of the mixture of epimeric 4-[5(R)-ethyl(or vinyl)-4(S)-quinuclidin-2ξ-ylcarbonyl]quinolines of formula VI, enantiomers or racemates thereof, to α(R)-[5(R)-ethyl(or vinyl)-4(S)-quinuclidin-2(S)-yl]-4-quinolinemethanols of formula I, enantiomer or racemate thereof, and to α(S)-[5(R)-ethyl(or vinyl)-4(S)-quinuclidin-2(R)-yl]-4-quinolinemethanols of formula II, enantiomer or racemate, respectively, is carried out utilizing a stereoselective reducing agent, for example, a dialkyl-aluminum hydride, such as diisobutyl-aluminum hydride or the like. The reduction is suitably carried out at room temperature; however, temperatures above or below room temperature may be employed. It is preferred to employ a temperature between 20°C. and 50°C. The reduction can be conveniently conducted in the presence of an inert organic solvent, for example, a hydrocarbon such as benzene or toluene, or an ether such as diethylether, tetrahydrofuran or the like. The compounds of formula I are then recovered from the reaction mixture utilizing conventional procedures, for example, crystallization and the like.

Exemplary of the compounds of formulas I and II are:
2,8-bis(trifluoromethyl)-α(R)-[5(R)-ethyl-4(S)-quinuclidin-2(S)-yl]-4-quinolinemethanol [also referred to hereinafter as 2′,8′-bis(trifluoromethyl)dihydrocinchonidine] and racemate thereof;

2,8-bis(trifluoromethyl)-α(S)-[5(S)-ethyl-4(R)-quinuclidin-2(R)-yl]-4-quinolinemethanol [also referred to as enantiomer of 2′,8′-bis(trifluoromethyl)-dihydrocinchonidine];

2,8-bis(trifluoromethyl)-α(S)-[5(R)-ethyl-4(S)-quinuclidin-2(R)-yl]-4-quinolinemethanol [also referred to as 2′,8′-bis(trifluoromethyl)dihydrocinchonine] and racemate thereof;

2,8-bis(trifluoromethyl)-α(R)-[5(S)-ethyl-4(R)-quinuclidin-2(S)-yl]-4-quinolinemethanol [also referred to as enantiomer of 2′,8′-bis(trifluoromethyl)-dihydrocinchonine];

2,8-bis(trifluoromethyl)-α(R)-[5(R)-vinyl-4(S)-quinuclidin-2(S)-yl]-4-quinolinemethanol [also referred to as 2′,8′-bis(trifluoromethyl)cinchonidine]; its enantiomer and racemates thereof;

2,8-bis(trifluoromethyl)-α(S)-[5(R)-vinyl-4(S)-quinuclidin-2(R)-yl]-4-quinolinemethanol [also referred to as 2′,8′-bis(trifluoromethyl)cinchonine]; its enantiomer and racemate thereof;

2,8-bis(trifluoromethyl)-α(S)-[5(R)-ethyl-4(S)-quinuclidin-2(S)-yl]-4-quinolinemethanol [also referred to as 2′,8′-bis(trifluoromethyl)-9-epi-dihydrocinchonidine] its enantiomer and racemate thereof;

2,8-bis(trifluoromethyl)-α(R)-[5(R)-ethyl-4(S)-quinuclidin-2(S)-yl]-4-quinolinemethanol [also referred to as 2',8'-bis(trifluoromethyl)-9-epi-dihydrocinchonine] its enantiomer and racemate thereof;

2,7-bis(trifluoromethyl)-α(R)-[5(R)-ethyl-4(S)-quinuclidin-2(S)-yl]-4-quinolinemethanol [also referred to as 2',7'-bis(trifluoromethyl)dihydrocinchonidine] its enantiomer and racemate thereof;

2,7-bis(trifluoromethyl)-α(S)-[5(R)-ethyl-4(S)-quinuclidin-2(R)-yl]-4-quinolinemethanol [also referred to as 2',7'-bis(trifluoromethyl)dihydrocinchonine] its enantiomer and racemate thereof;

2,7-bis(trifluoromethyl)-α(S)-[5(R)-ethyl-4(S)-quinuclidin-2(S)-yl]-4-quinolinemethanol [also referred to as 2',7'-bis(trifluoromethyl)-9-epi-dihydrocinchonidine] its enantiomer and racemate thereof;

2,7-bis(trifluoromethyl)-α(R)-[5(R)-ethyl-4(S)-quinuclidin-2(R)-yl]-4-quinolinemethanol [also referred to as 2',7'-bis(trifluoromethyl)-9-epi-dihydrocinchonine] its enantiomer and racemate thereof;

2,5-bis(trifluoromethyl)-α(R)-[5(R)-ethyl-4(S)-quinuclidin-2(S)-yl]-4-quinolinemethanol [also referred to as 2',5'-bis(trifluoromethyl)dihydrocinchonidine] its enantiomer and racemate thereof;

2,5-bis(trifluoromethyl)-α(S)-[5(R)-ethyl-4(S)-quinuclidin-2(R)-yl]-4-quinolinemethanol [also referred to as 2',7'-bis(trifluoromethyl)dihydrocinchonine] its enantiomer and racemate thereof;

2,5-bis(trifluoromethyl)-α(S)-[5(R)-ethyl-4(S)-quinuclidin-2(S)-yl]-4-quinolinemethanol [also referred to as 2',5'-bis(trifluoromethyl)-9-epi-dihydrocinchonidine] its enantiomer and racemate thereof;

2,5-bis(trifluoromethyl)-α(R)-[5(R)-ethyl-4(S)-quinuclidin-2(R)-yl]-4-quinolinemethanol [also referred to as 2',5'-bis(trifluoromethyl)-9-epi-dihydrocinchonine] its enantiomer and racemate thereof;

2,6-bis(trifluoromethyl)-α(R)-[5(R)-ethyl-4(S)-quinuclidin-2(S)-yl]-4-quinolinemethanol [also referred to as 2',6'-bis(trifluoromethyl)dihydrocinchonidine] its enantiomer and racemate thereof;

2,6-bis(trifluoromethyl)-α(S)-[5(R)-ethyl-4(S)-quinuclidin-2(R)-yl]-4-quinolinemethanol [also referred to as 2',6'-bis(trifluoromethyl)dihydrocinchonine] its enantiomer and racemate thereof;

2,6-bis(trifluoromethyl)-α(S)-[5(R)-ethyl-4(S)-quinuclidin-2(S)-yl]-4-quinolinemethanol [also referred to as 2',6'-bis(trifluoromethyl)-9-epi-dihydrocinchonidine] its enantiomer and racemate thereof;

2,6-bis(trifluoromethyl)-α(R)-[5(R)-ethyl-4(S)-quinuclidin-2(R)-yl]-4-quinolinemethanol [also referred to as 2',6'-bis(trifluoromethyl)-9-epi-dihydrocinchonine] its enantiomer and racemate thereof;

8-chloro-2-trifluoromethyl-α(R)-[5(R)-ethyl-4(S)-quinuclidin-2(S)-yl]-4-quinolinemethanol [also referred to as 8'-chloro-2'-trifluoromethyl-dihydrocinchonidine] its enantiomer and racemate thereof;

8-chloro-2-trifluoromethyl-α(S)-[5(R)-ethyl-4(S)-quinuclidin-2(R)-yl]-4-quinolinemethanol [also referred to as 8'-chloro-2'-trifluoromethyl-dihydrocinchonine] its enantiomer and racemate thereof;

8-chloro-2-trifluoromethyl-α(S)-[5(R)-ethyl-4(S)-quinuclidin-2(S)-yl]-4-quinolinemethanol [also referred to as 8'-chloro-2'-trifluoromethyl-9-epi-dihydrocinchonidine] its enantiomer and racemate thereof;

8-chloro-2-trifluoromethyl-α(R)-[5(R)-ethyl-4(S)-quinuclidin-2(R)-yl]-4-quinolinemethanol [also referred to as 8'-chloro-2'-trifluoromethyl-9-epi-dihydrocinchonine] its enantiomer and racemate thereof;

5-chloro-2-trifluoromethyl-α(R)-[5(R)-ethyl-4(S)-quinuclidin-2(S)-yl]-4-quinolinemethanol [also referred to as 5'-chloro-2'-trifluoromethyl-dihydrocinchonidine] its enantiomer and racemate thereof;

5-chloro-2-trifluoromethyl-α(S)-[5(R)-ethyl-4(S)-quinuclidin-2(R)-yl]-4-quinolinemethanol [also referred to as 5'-chloro-2'-trifluoromethyl-dihydrocinchonine] its enantiomer and racemate thereof;

5-chloro-2-trifluoromethyl-α(S)-[5(R)-ethyl-4(S)-quinuclidin-2(S)-yl]-4-quinolinemethanol [also referred to as 5'-chloro-2'-trifluoromethyl-9-epidihydrocinchonidine] its enantiomer and racemate thereof;

5-chloro-2-trifluoromethyl-α(R)-[5(R)-ethyl-4(S)-quinuclidin-2(R)-yl]-4-quinolinemethanol [also referred to as 5'-chloro-2'-trifluoromethyl-9-epi-dihydrocinchonine] its enantiomer and racemate thereof;

6-chloro-2-trifluoromethyl-α(R)-[5(R)-ethyl-4(S)-quinuclidin-2(S)-yl]-4-quinolinemethanol [also referred to as 6'-chloro-2'-trifluoromethyl-dihydrocinchonidine] its enantiomer and racemate thereof;

6-chloro-2-trifluoromethyl-α(S)-[5(R)-ethyl-4(S)-quinuclidin-2(R)-yl]-4-quinolinemethanol [also referred to as 6'-chloro-2'-trifluoromethyl-dihydrocinchonine] its enantiomer and racemate thereof;

6-chloro-2-trifluoromethyl-α(S)-[5(R)-ethyl-4(S)-quinuclidin-2(S)-yl]-4-quinolinemethanol [also referred to as 6'-chloro-2'-trifluoromethyl-9-epi-dihydrocinchonidine] its enantiomer and racemate thereof;

6-chloro-2-trifluoromethyl-α(R)-[5(R)-ethyl-4(S)-quinuclidin-2(R)-yl]-4-quinolinemethanol [also referred to as 6'-chloro-2'-trifluoromethyl-9-epi-dihydrocinchonine] its enantiomer and racemate thereof;

7-chloro-2-trifluoromethyl-α(R)-[5(R)-ethyl-4(S)-quinuclidin-2(S)-yl]-4-quinolinemethanol [also referred to as 7'-chloro-2'-trifluoromethyl-dihydrocinchonidine] its enantiomer and racemate thereof;

7-chloro-2-trifluoromethyl-α(S)-[5(R)-ethyl-4(S)-quinuclidin-2(R)-yl]-4-quinolinemethanol [also referred to as 7'-chloro-2'-trifluoromethyl-dihydrocinchonine] its enantiomer and racemate thereof;

7-chloro-2-trifluoromethyl-α(S)-[5(R)-ethyl-4(S)-quinuclidin-2(S)-yl]-4-quinolinemethanol [also referred to as 7'-chloro-2'-trifluoromethyl-9-epi-dihydrocinchonidine] its enantiomer and racemate thereof;

7-chloro-2-trifluoromethyl-α(R)-[5(R)-ethyl-4(S)-quinuclidin-2(R)-yl]-4-quinolinemethanol [also referred to as 7'-chloro-2'-trifluoromethyl-9-epi-dihydrocinchonine] its enantiomer and racemate thereof.

A preferred compound of the invention is racemic 2',8'-bis(trifluoromethyl)dihydrocinchonine.

Exemplary of the compounds of formula IV are the following:

2,7-bis(trifluoromethyl)-4-quinolyllithium;
2,8-bis(trifluoromethyl)-4-quinolyllithium;
8-chloro-2-trifluoromethyl-4-quinolyllithium;
7-chloro-2-trifluoromethyl-4-quinolyllithium;
2,6-bis(trifluoromethyl)-4-quinolyllithium;
2,5-bis(trifluoromethyl)-4-quinolyllithium;
5-chloro-2-trifluoromethyl-4-quinolyllithium;
6-chloro-2-trifluoromethyl-4-quinolyllithium; and the like.

Since the foregoing 4-quinolyllithium compounds are highly labile, it is preferred to prepare then in situ, by reacting the corresponding 4-bromoquinoline with, for example, n-butyllithium in the presence of a solvent, for example, a hydrocarbon, such as benzene, toluene, hexane, petroleum ether; or an ether, such as dioxane, ether, diglyme, tetrahydrofuran, and the like. Exemplary of the 4-bromoquinoline compounds are:

2,7-bis(trifluoromethyl)-4-bromoquinoline;
2,8-bis(trifluoromethyl)-4-bromoquinoline;
2,6-bis(trifluoromethyl)-4-bromoquinoline;
2,5-bis(trifluoromethyl)-4-bromoquinoline;
4-bromo-8-chloro-2-trifluoromethylquinoline;
4-bromo-7-chloro-2-trifluoromethylquinoline;
4-bromo-5-chloro-2-trifluoromethylquinoline;
4-bromo-6-chloro-2-trifluoromethylquinoline; and the like.

The 4-haloquinolines can be prepared by known procedures from the corresponding 4-hydroxyquinolines, exemplary of which are:

2,7-bis(trifluoromethyl)-4-quinolinol;
2,8-bis(trifluoromethyl)-4-quinolinol;
2,6-bis(trifluoromethyl)-4-quinolinol;
2,5-bis(trifluoromethyl)-4-quinolinol;
8-chloro-2-trifluoromethy-4-quinolinol;
7-chloro-2-trifluoromethyl-4-quinolinol;
5-chloro-2-trifluoromethyl-4-quinolinol;
6-chloro-2-trifluoromethyl-4-quinolinol; and the like.

The compounds of formulas I and II and their pharmaceutically acceptable acid addition salts possess antimalarial properties and are therefore useful as antimalarial agents.

The pharmacologically useful antimalarial activity of the aforementioned compounds is demonstrated in warm-blooded animals using standard procedures, for example, the test substance is administered to albino mice in variable amounts. Albino mice are inoculated with about 10 million red cells infected with $P.$ $berghei$. Treatment is started on the first day after inoculation, and the drug is administered "per os" during four consecutive days. On the seventh day of infection, smears are made, stained with giemsa and microscopically examined for $P.$ $berghei$.

When racemic 2′,8′-bis(trifluoromethyl)-dihydrocinchonidine and racemic 2′,8′-bis(trifluoromethyl)-dihydrocinchonine, which have demonstrated I.P. an $LD_{50}$ in the range of 800–900 mg/kg., are utilized as the test substance at dosages in the range of 6 mg/kg. to about 25 mg/kg., the microscopical examination of the blood smears is free of $P.$ $berghei$ (negative).

The compounds of formulas I and II have effects qualitatively similar, for example, to those of quinine and quinidine of known therapeutic uses and properties. Thus, the compounds prepared by the process of the invention demonstrate a pattern of activity associated with antimalarials of known efficacy and safety.

The compounds of formulas I and II form pharmaceutically acceptable acid addition salts and such salts are also within the scope of this invention. Thus, the aforementioned compounds form pharmaceutically acceptable addition salts with, for example, both pharmaceutically acceptable organic and inorganic acids, such as acetic acid, succinic acid, formic acid, methanesulfonic acid, p-toluenesulfonic acid, hydrochloric acid, nitric acid, phosphoric acid, sulfuric acid, and the like.

The compounds of formulas I and II of the invention can be incorporated into standard pharmaceutical dosage forms, for example, they are useful for oral or parenteral application with the usual pharmaceutical adjuvant materials, e.g., organic or inorganic inert carrier materials such as water, gelatin, lactose, starch, magnesium stearate, talc, vegetable oils, gums, polyalkyleneglycols, and the like. The pharmaceutical preparations can be employed in a solid form, e.g., as tablets, troches, suppositories, capsules, or in liquid form, e.g., as solutions, suspensions or emulsions. The pharmaceutical adjuvant materials can include preservatives, stabilizers, wetting or emulsifying agents, salts to change the osmotic pressure or to act as buffers. They can also contain other therapeutically active materials.

The following Examples further illustrate the invention. All temperatures are stated in degrees Centigrade, unless otherwise mentioned.

EXAMPLE 1

Preparation of 2,7-bis(trifluoromethyl)-4-quinolinol and 2,5-bis(trifluoromethyl)-4-quinolinol To a solution of 60 g. of ethyl 4,4,4-trifluoroacetoacetate in 200 ml. of polyphosphoric acid, preheated to 100°, was added dropwise 52.7 g. of 3-trifluoromethylaniline. Following the addition, the mixture was stirred at 140°–150° for 2 hours. After standing at room temperature overnight, the reaction mixture was poured into 1 liter of ice-water with vigorous stirring. The precipitate was collected by filtration and washed thoroughly with water. The dried material was taken up in ether. Insolubles were removed by filtration, and the filtrate, after drying over sodium sulfate, was evaporated to dryness under reduced pressure to yield 62.7 g. of a mixture of 2,7-bis(trifluoromethyl)-4-quinolinol and 2,5-bis(trifluoromethyl)-4-quinolinol. Part of this material was recrystallized several times from ethanol to yield analytically pure 2,5-bis(trifluoromethyl)-4-quinolinol in the form of white needles, m.p. 314°–315°.

Analysis Calcd. for $C_{11}H_5F_6NO$: C, 46.99; H, 1.79; N, 4.98; F, 40.55. Found: C, 47.19; H, 1.70; N, 5.05; F, 40.66.

The mother liquor of the crystallization of 2,5-bis(trifluoromethyl)-4-quinolinol was evaporated to dryness and part of the residue was sublimed at 150°–160° and 0.1 mm. of mercury. The sublimate was recrystallized from acetone to afford pure 2,7-bis(trifluoromethyl)-4-quinolinol, m.p. 184°–185°C.

Analysis Calcd. for: $C_{11}H_5F_6NO$: C, 46.99; H, 1.79; N, 4.98; F, 40.55. Found: C, 47.03; H, 2.00; N, 5.05; F, 40.56.

EXAMPLE 2

Preparation of 2,7-bis(trifluoromethyl)-4-bromoquinoline and 2,5-bis(trifluoromethyl)-4-bromoquinoline To a slurry of 27 g. of a mixture of 2,5-bis(trifluoromethyl)-4-quinolinol and 2,7-bis(trifluoromethyl)-4-quinolinol and 40 ml. of phosphorus tribromide, preheated to 70°, was added 27 ml. of phosphorus oxybromide. The mixture was heated at 140° for 4 hours. Thereafter, the mixture was cooled to room temperature, carefully added to 2 liters of vigorously stirred crushed ice and rendered alkaline by the addition of 10N sodium hydroxide. The precipitate which formed was separated from the aqueous layer by decantation and taken up in dichloromethane. Insolubles were removed by filtration. The filtrate was dried over sodium sulfate and evaporated to dryness under reduced pressure. The tan solid residue (24.6 g.) was chromatographed on 1 kg. of silica gel with hexane-benzene (8:2) as the eluent. Fractions of 200 ml. were collected and the progress of the chromatography was monitored by thin layer chromatography (silica gel, hexane-benzene 8:2). Fractions 6–17 were combined and after removal of the solvent yielded 13.5 g. of white solid 2,7-bis(trifluoromethyl)-4-bromoquinoline, m.p. 100°–101°.

Analysis Calcd. for $C_{11}H_4BrF_6N$: C, 38.40; H, 1.17; N, 4.07; F, 33.13. Found: C, 38.37; H, 1.10; N, 4.15; F, 33.05.

After collecting 3 fractions containing a mixture of bromides, elution with 4 liters of solvent gave 7.7 g. of a clear yellow oil, which solidified on standing. Crystallization from hexane yielded pure 2,5-bis(trifluoromethyl)-4-bromoquinoline, m.p. 48°–50°.

Analysis Calcd. for $C_{11}H_4BrF_6N$: C, 38.40; H, 1.17; N, 4.07; F, 33.13. Found: C, 38.43; H, 1.06; N, 4.11; F, 33.03.

EXAMPLE 3

Preparation of racemic 2',7'-bis(trifluoromethyl)-dihydrocinchonidine and racemic 2',7'-bis(trifluoromethyl)-dihydrocinchonine To 500 ml. of anhydrous ether was added 55 ml. of a 1.6M solution of butyllithium in hexane. The resulting solution was cooled to −70° and with stirring 30 g. of 2,7-bis(trifluoromethyl)-4-bromoquinoline dissolved in 200 ml. of anhydrous ether was added under an atmosphere of nitrogen at such a rate as to maintain a temperature of −70°. Stirring of the solution containing the 2,7-bis(trifluoromethyl)-4-quinolyllithium which formed was continued at this temperature for 30 minutes, followed by the addition of 15.17 g. of racemic 4,5-erythro-5-ethylquinuclidine-2ξ-carboxaldehyde dissolved in 100 ml. of anhydrous ether. The reaction mixture was stirred at −70° for an additional 3.5 hours. Then, it was quenched with water, diluted with 500 ml. of ether and allowed to warm to room temperature. The ethereal solution was washed twice with water, dried over sodium sulfate and evaporated to dryness to yield 44.4 g. of crude product. Separation and purification was achieved by column chromatography (i.d. 60 mm) on silica gel (2 kg.) with chloroform-acetone-triethylamine (5:4:1) as the liquid phase. Fractions of 150 ml. were collected and the progress of the chromatography was monitored by tlc on silica gel with the same solvent mixture. Combined fractions were evaporated to dryness. After an initial empty forerun of 2550 ml., the next 750 ml. yielded 14.5 g. of an oily solid (mostly unreacted starting materials) followed by 6.7 g. of a mixture of the 9-epi-derivatives of racemic 2',7'-bis(trifluoromethyl)-dihydrocinchonidine and racemic 2',7'-bis(trifluoromethyl)-dihydrocinchonine (from 2.7 liters). After empty fractions totaling 2.4 liters, continuation of the chromatography yielded 4 g. of a white solid from the next 4.1 liters. Recrystallization from ethanol yielded analytically pure racemic 2',7'-bis(trifluoromethyl)dihydrocinchonine, m.p. 201°–203°.

Analysis Calcd. for $C_{21}H_{22}F_6N_2O$: C, 58.34; H, 5.13; N, 6.48; F, 26.35. Found: C, 58.51; H, 5.05; N, 6.55; F, 26.58.

After another 1.2 liters containing a mixture of racemic 2',7'-bis(trifluoromethyl)-dihydrocinchonidine and racemic 2',7'-bis(trifluoromethyl)-dihydrocinchonine, the final 7 liters yielded 6.8 g. of near white solid. Recrystallization from ethanol yielded 1.4 g. of pure racemic 2',7'-bis(trifluoromethyl)dihydrocinchonidine, m.p. 221°–222°.

Analysis Calcd. for $C_{21}H_{22}F_6N_2O$: C, 58.34; H, 5.13; N, 6.48; F, 26.35. Found: C, 38.36; H, 5.02; N, 6.52; F, 26.29.

EXAMPLE 4

Preparation of 4-bromo-8-chloro-2-trifluoromethylquinoline

To a slurry of 35 g. of 8-chloro-2-trifluoromethyl-4-quinolinol in 70 ml. of phosphorus tribromide, preheated to 70°, was added 35 ml. of phosphorus oxybromide. The reaction mixture was heated at 140° for 4 hours with occasional manual stirring. The mixture was cooled to room temperature and carefully added to 2 liters of vigorously stirred crushed ice. The aqueous suspension was rendered alkaline by the addition of 10N sodium hydroxide and the temperature was kept low by the addition of more ice when needed. The precipitate was collected by filtration and washed thoroughly with water. The air-dried filter cake (48 g.) was sublimed at 100° and 0.5 mm. mercury to yield 40.2 g. of white 4-bromo-8-chloro-2-trifluoromethylquinoline, which upon recrystallization from ethanol gave analytically pure 4-bromo-8-chloro-2-trifluoromethylquinoline, m.p. 62°–64°.

Analysis Calcd. for $C_{10}H_4BrClF_3N$: C, 38.68; H, 1.30; N, 4.51; F, 18.35. Found: C, 38.53; H, 1.23; N, 4.60; F, 18.06.

EXAMPLE 5

Preparation of racemic 8'-chloro-2'-trifluoromethyl-dihydrocinchonidine and racemic 8'-chloro-2'-trifluoromethyl-dihydrocinchonine To 600 ml. of anhydrous ether was added 87 ml. of a 1.6M solution of butyllithium in hexane. The resulting solution was cooled to −70° and with stirring 39 g. of 4-bromo-8-chloro-2-trifluoromethylquinoline dissolved in 200 ml. of anhydrous ether was added under an atmosphere of nitrogen at such a rate as to maintain a temperature of −70°. Stirring of the solution containing the 8-chloro-2-trifluoromethyl-4-quinolyllithium was continued at this temperature for 30 minutes followed by the addition of 23.2 g. of racemic 4,5-erythro-5-ethylquinuclidine-2ξ-carboxaldehyde dissolved in 100 ml. of anhydrous ether. The reaction mixture was stirred at −70° overnight. Then, it was quenched with water, diluted with 500 ml. of ether and allowed to warm to room temperature. The ethereal solution was washed twice with water, dried over sodium sulfate and evaporated to dryness to yield 52.5 g. of a brown foamy material. The crude product was purified by column chromatography (i.d. 60 mm) on silica gel. After an initial empty forerun of 5 liters (solvent: chloroform-acetone-triethylamine 7:2:1) the ratio was changed to 4:5:1 and fractions of 150 ml. were collected. The progress of the chromatography was monitored by tlc on silica gel with the same solvent mixture. Combined fractions were evaporated and the residue was dissolved in dichloromethane. The organic solution was washed with water. The aqueous layer was backwashed with dichloromethane, and the combined organic solution was dried over sodium sulfate and evaporated under reduced pressure. After 17 empty fractions (2.5 liters), the next 750 ml. yielded 7.9 g. of a brown oil (mostly unreacted starting materials) followed by 20.3 g of a mixture of the 9-epi-derivatives of racemic 8'-chloro-2'-trifluoromethyl-dihydrocinchonidine and racemic 8'-chloro-2'-trifluoromethyl-dihydrocinchonine (from 2.25 liters). After another interval of empty fractions totaling 5.5 liters, the next 6 liters of the above solvent and 4.5 liters of acetone-triethylamine (9:1) eluded 15.3 g. of a mixture of racemic 8'-chloro-2'-trifluoromethyl-dihydrocinchonidine and racemic 8'-chloro-2'-trifluoromethyl-dihydrocinchonine. Crystallization from benzene-petroleum ether yielded 6.1 g. of racemic 8'-chloro-2'-trifluoromethyl-dihydrocinchonidine, m.p. 234–236° after two recrystallizations from acetone.

Analysis Calcd. for $C_{20}H_{22}ClF_3N_2O$: C, 60.20; H, 5.56; N, 7.01; F, 14.29. Found: C, 60.22; H, 5.51; N, 7.03; F, 14.49.

Concentration of the mother liquor afforded 4.5 g. of racemic 8'-chloro-2'-trifluoromethyl-dihydrocinchonine, m.p. 194–196° after two recrystallizations from acetone.

Analysis Calcd. for $C_{20}H_{22}ClF_3N_2O$: C, 60.20; H, 5.56; N, 7.02; F, 14.29. Found: C, 60.24; H, 5.50; N, 7.03; F, 14.52.

EXAMPLE 6

Preparation of 7-chloro-2-trifluoromethyl-4-quinolinol and 5-chloro-2-trifluoromethyl-4-quinolinol To a solution of 60 g. of ethyl 4,4,4-trifluoroacetoacetate in 200 ml. of polyphosphoric acid, preheated to 100°, was added dropwise 42 g. of 3-chloroaniline. Following the addition, the mixture was stirred at 140°–150° for 2 hours. After standing at room temperature overnight, the reaction mixture was poured into 500 ml. of ice-water with vigorous stirring. The precipitate was collected by filtration and washed thoroughly with water. To assure dryness, the filter cake was repeatedly suspended in ethanol-benzene followed by removal of the solvent under reduced pressure. The dried crude product was extracted three times with 1 liter of hot ether each. The extracts were combined and, after removal of the solvents, yielded 76 g. of a mixture of 7-chloro-2-trifluoromethyl-4-quinolinol and 5-chloro-2-trifluoromethyl-4-quinolinol. Crystallization of this mixture from ethanol yielded a light yellow solid. Fractional crystallization from ethyl acetate yielded 7-chloro-2-trifluoromethyl-4-quinolinol in small white clusters of needles, m.p. 310°–312°.

Analysis Calcd. for $C_{10}H_5ClF_3NO$: C, 48.51; H, 2.03; N, 5.66; F, 23.02. Found: C, 48.51; H, 2.03; N, 5.66; F, 23.02.

Concentration of the mother liquord of the crystallization of 7-chloro-2-trifluoromethyl-4-quinolinol yielded 5-chloro-2-trifluoromethyl-4-quinolinol in the form of colorless cubes, m.p. 242°–244°, after several crystallizations from ethyl acetate.

Analysis Calcd. for $C_{10}H_5ClF_3NO$: C, 48.51; H, 2.03; N, 5.66; F, 23.02. Found: C, 48.33; H, 1.97; N, 5.77; F, 23.21.

EXAMPLE 7

Preparation of 4-bromo-7-chloro-2-trifluoromethylquinoline and 4-bromo-5-chloro-2-trifluoromethylquinoline To a slurry of 50 g. of a mixture of 7-chloro-2-trifluoromethyl-4-quinolinol and 5-chloro-2-trifluoromethyl-4-quinolinol in 100 ml. of phosphorus tribromide, preheated to 70°, was added in one portion 50 ml. of phosphorus oxybromide. The mixture was heated at 140° for 4 hours. The mixture was cooled to room temperature and carefully added to 2 liters of vigorously stirred crushed ice. The aqueous suspension was rendered alkaline by the addition of 10N sodium hydroxide and the temperature was kept low by the addition of more ice as required. The brown precipitate was collected by filtration, washed thoroughly with water and air-dried. Sublimation at 110° and 0.1 mm. mercury, yielded 50 g. of a mixture of 4-bromo-7-chloro-2-trifluoromethylquinoline and 4-bromo-5-chloro-2-trifluoromethylquinoline. Separation was achieved by chromatography on silica gel (1 kg., i.d. of column 60 mm) with hexane-benzene (8:2) as the liquid phase. Fractions of 200 ml. were collected and the progress of the chromatography was monitored by tlc (silica gel, hexane-benzene 8:2). After an empty forerun of 1.2 liters, fractions 7-12 were combined and removal of the solvent yielded 13.1 g. of 4-bromo-7-chloro-2-trifluoromethylquinoline, m.p. 68°–70° after recrystallization from ethanol.

Analysis Calcd. for $C_{10}H_4BrClF_3N$: C, 38.68; H, 1.30; N, 4.51; F, 18.35. Found: C, 38.62; H, 1.16; N, 4.46; F, 18.39.

After collecting 600 ml. containing 7 g. of a mixture of 4-bromo-7-chloro-2-trifluoromethylquinoline and 4-bromo-5-chloro-2-trifluoromethylquinoline, elution with 4.4 liters gave 27.3 g. of 4-bromo-5-chloro-2-trifluoromethylquinoline, m.p. 98°–100° after recrystallization from ethanol.

Analysis Calcd. for $C_{10}H_4BrClF_3N$: C, 38.68; H, 1.30; N, 4.51; F, 18.35. Found: C, 38.62; H, 1.16; N, 4.46; F, 18.39.

EXAMPLE 8

Preparation of racemic 7'-chloro-2'-trifluoromethyl-dihydrocinchonidine and racemic 7'-chloro-2'-trifluoromethyl-dihydrocinchonine To 75 ml. of anhydrous ether was added 12.5 ml. of a 1.6M solution of butyllithium in hexane. The resulting solution was cooled to −70° and with stirring 5.3 g. of 4-bromo-7-chloro-2-trifluoromethylquinoline dissolved in 50 ml. of anhydrous ether was added under an atmosphere of nitrogen at such a rate as to maintain a temperature of −70°. Stirring of the solution containing the 7-chloro-2-trifluoromethyl-4-quinolyllithium was continued at this temperature for 30 minutes followed by the addition of 3.3 g. of racemic 4,5-erythro-5-ethyl-quinuclidine-2$\xi$-carboxaldehyde dissolved in 50 ml. of anhydrous ether. The reaction mixture was stirred at −70° for an additional 5 hours, hydrolyzed with water, diluted with 100 ml. of ether and allowed to warm to room temperature. The ethereal solution was washed twice with water, dried over sodium sulfate and evaporated to dryness to yield 6.1 g. of a yellow oil. This material was placed on a silica gel column (500 g. of silica gel, i.d. of column 20 mm) and eluted furst with chloroform-acetone-triethylamine (5:4:1, solvent A) (2.5 liters) followed by chloroform-acetone-triethylamine (4:6:1). Fractions of 50 ml. were collected and the progress of the chromatography was monitored by tlc on silica gel with solvent A as the liquid phase. The combined fractions were evaporated to dryness and the residue was dissolved in dichloromethane. The organic solution was washed with water, the aqueous layer was backwashed with dichloromethane, and the combined organic solution was dried over sodium sulfate and evaporated under reduced pressure. After 750 ml. of forerun, the next 300 ml. yielded 1.9 g. of a crude mixture of the 9-epi-derivatives of racemic 7'-chloro-2'-trifluoromethyl-dihydrocinchonidine and racemic 7'-chloro-2'-trifluoromethyl-dihydrocinchonine. Fractions 29–44 yielded 0.5 g. of racemic 7-chloro-2-trifluoromethyl-dihydrocinchonine. Two recrystallizations from acetone gave analytically pure racemic 7'-chloro-2'-trifluoromethyl-dihydrocinchonine, m.p. 203°–205° after drying at 100° under reduced pressure.

Analysis Calcd. for $C_{20}H_{22}ClF_3N_2O$: C, 60.22; H, 5.56; N, 7.02; F, 14.29. Found: C, 60,28; H, 5.52; N, 7.04; F, 14.23.

Continuation of the chromatography gave from fractions 45–70, 1.2 g. of racemic 7-chloro-2-trifluoromethyl-dihydrocinchonidine. Crystallization from acetone followed by recrystallization from ether-petroleum ether yielded pure racemic 7-chloro-2-trifluoromethyl-dihydrocinchonidine, m.p. 178°–180°.

Analysis Calcd. for $C_{20}H_{22}ClF_3N_2O$: C, 60.22; H, 5.56; N, 7.02; F, 14.29. Found: C, 60.22; H, 5.60; N, 7.03; F, 14.49.

EXAMPLE 9

Preparation of racemic 4,5-erythro-5-ethylquinuclidine-2ξ-carboxaldehyde

A solution containing 13.8 g. of a mixture of isomeric erythro 1,1-dichloro-3-[3-ethyl-4-piperidinyl]propan-2ξ-ol hydrochlorides in 125 ml. of water was combined with 1250 ml. of benzene. The stirred mixture was cooled in an ice bath and 81 ml. of a 1.85N potassium hydroxide solution was added slowly. Stirring at room temperature was continued under an atmosphere of nitrogen for 20 hours. The aqueous layer was separated and extracted with benzene. The combined organic layer was washed once with water, dried over sodium sulfate and evaporated under reduced pressure at 30°. The residue on bulb-to-bulb-distillation at 80° (bath temperature) and 0.1 mm. mercury, yielded 5.37 g. (64%) of liquid racemic epimeric 4,5-erythro-5-ethylquinuclidine-2ξ-carboxaldehyde.

An analytically pure sample of racemic epimeric 4,5-erythro-5-ethylquinuclidine-2ξ-carboxaldehyde was prepared as follows: the residue obtained from the reaction of 5.45 g. of the propanol derivative with potassium hydroxide as above was dissolved in 100 ml. of anhydrous ether. The solution was added to 2.5 g. of sodium bisulfite in 8 ml. of water. The solvents were removed under reduced pressure, and the residue was dissolved in 10 ml. of water. Addition of ethanol followed by the addition of ether precipitated 3.4 g. of solid addition product. This product was added to 50 ml. of a saturated aqueous solution of sodium carbonate and heated at 40°. After all material had dissolved, the solution was kept at 40° for another 5 minutes. The mixture was cooled and extracted three times with ether. The combined ether extracts were dried over potassium carbonate and evaporated to dryness under reduced pressure to give 950 mg. of liquid racemic 4,5-erythro-5-ethylquinuclidine-2ξ-carboxaldehyde. Distillation in a short path distillation apparatus at 60°–85° (oil bath temperature) under a pressure of 0.4 mm. mercury gave 648 mg. of analytically pure racemic 4,5-erythro-5-ethylquinuclidine-2ξ-carboxaldehyde.

Analysis Calcd. for $C_{10}H_{17}NO$: C, 71.81; H, 10.25; N, 8.38. Found: C, 71.91; H, 10.02; N, 8.58.

EXAMPLE 10

Preparation of 2,8-bis(trifluoromethyl)-4-bromoquinoline

A suspension of 25.5 g. of 2,8-bis(trifluoromethyl)-4-hydroxyquinoline in 50 ml. phosphorus tribromide was heated to 70°. In one portion 70 g. (25 ml.) of phosphorus oxybromide was added. The temperature was raised to 140° and the mixture was kept at this temperature for 4 hours. After the mixture was cooled to room temperature, 1 liter of crushed ice was added carefully with vigorous stirring. Additional ice was added, as necessary, until the exothermic reaction ceased. The solution was rendered alkaline with 12N sodium hydroxide and ice was again added for cooling. The yellow solid precipitate was collected by filtration and air-dried overnight. Sublimation at 50° and 0.2 mm. mercury yielded 28.6 g. (92%) of 2,8-bis(trifluoromethyl)-4-bromoquinoline, m.p. 57°–58°. For analytical purposes, 1 g. of the sublimed material was recrystallized from 95% ethanol to afford 0.7 g. of analytically pure 2,8-bis(trifluoromethyl)-4-bromoquinoline, m.p. 59°–60°.

Analysis Calcd. for $C_{11}H_4BrF_6N$: C, 38.40; H, 1.17; N, 4.07; F, 33.13. Found: C, 38.45; H, 1.05; N, 4.15; F, 33.34.

EXAMPLE 11

Preparation of racemic 2',8'-bis(trifluoromethyl)dihydrocinchonidine and racemic 2',8'-bis(trifluoromethyl)dihydrocinchonine To 200 ml. of anhydrous ether was added 20 ml. of a 1.6M solution of butyllithium in hexane. The resulting solution was cooled to −70° and with stirring under nitrogen 11.0 g. of 2,8-bis(trifluoromethyl)-4-bromoquinoline dissolved in 200 ml. of anhydrous ether was added at such a rate as to maintain a low reaction temperature. Stirring was continued at −70° for another 15 minutes followed by the addition of 5.35 g. of racemic 4,5-erythro-5-ethylquinuclidine-2ξ-carboxaldehyde dissolved in 100 ml. of anhydrous ether. The reaction mixture was stirred for an additional 1.5 hours, then quenched with water (10 ml.), diluted with 500 ml. of ether and allowed to warm up to room temperature. The ethereal solution was washed with water (100 ml.), dried over sodium sulfate and evaporated under reduced pressure to yield 14.2 g. of an oil. The same reaction was carried out under identical conditions with 9.35 g. of 2,8-bis(trifluoromethyl)-4-bromoquinoline and 4.53 g. of racemic 4,5-erythro-5-ethylquinuclidine-2ξ-carboxaldehyde to yield 13 g. of crude product. Both were combined and chromatographed on 2 kg. (column i.d. 60 mm) of silica gel with chloroform-acetone-triethylamine (5:4:1) as the solvent. Fractions of 125 ml. were collected. The progress of the chromatography was monitored by tlc on silica gel with the same solvent. Combined fractions were evaporated and the residue was dissolved in dichloromethane. The organic solution was washed with water, the aqueous layer was backwashed with dichloromethane, and the combined organic solution was dried over sodium sulfate and evaporated under reduced pressure.

After an initial empty forerun of 1125 ml., the next 1250 ml. yielded 5.9 g. of an orange oil (mostly unreacted starting materials), followed by 10.1 g. of a yellow oil from 4.25 liters). Crystallization of this material from ether yielded 3 g. of white powdery racemic 2′,8′-bis(trifluoromethyl)-9-epi-dihydrocinchonine, m.p. 166°–168°.

Analysis Calcd. for $C_{21}H_{22}F_6N_2O$: C, 58.34; H, 5.13; N, 6.48; F, 26.35. Found: C, 58.16; H, 5.11; N, 6.43; F, 26.40.

The mother liquor of the crystallization of racemic 2′,8′-bis(trifluoromethyl)-9-epi-dihydrocinchonine was evaporated and the oily residue was dissolved in ethanolic hydrochloric acid, and the solution was diluted with ether. The precipitated oil crystallized upon standing to yield 2.4 g. of a white solid, m.p. 249°–252°. Part of this material (0.2 g.) was treated with 1N sodium hydroxide and the free base was extracted into dichloromethane. The extract was dried over sodium sulfate and removal of the solvent under reduced pressure yielded a yellow oil. Crystallization from benzene-petroleum ether (30°–60°) yielded 78 mg. of racemic 2′,8′-bis(trifluoromethyl)-9-epi-dihydrocinchonidine, m.p. 149°–150°.

Analysis Calcd. for $C_{21}H_{22}F_6N_2O$: C, 58.34; H, 5.13; N, 6.48; F, 26.35. Found: C, 58.30; H, 5.03; N, 6.49; F, 26.30.

Continuation of the chromatography afforded after empty fractions totaling 6.2 liters, 4.3 g. of yellow oil from the next 11.9 liters. The crude product on crystallization from chloroform yielded 2.2 g. of a white solid, m.p. 208°–210°, which on recrystallization from chloroform-ether yielded pure racemic 2′,8′-bis(trifluoromethyl)dihydrocinchonine, m.p. 213°–215° after drying at 100° for 20 hours in high vacuum.

Analysis Calcd. for $C_{21}H_{22}F_6N_2O$: C, 58.34; H, 5.13; N, 6.48; F, 26.35. Found: C, 58.21; H, 5.13; N, 6.34; F, 26.41.

After another 15.6 liters containing 1.2 g. of a mixture of racemic 2′,8′-bis(trifluoromethyl)dihydrocinchonidine and racemic 2′,8′-bis(trifluoromethyl)-dihydrocinchonine, the final 12.5 liters afforded 2.6 g. of crude product. Crystallization from ether yielded 1.9 g. of white solid, m.p. 217°–219° which on recrystallization from methanol gave pure racemic 2′,8′-bis(trifluoromethyl)-dihydrocinchonidine, m.p. 225°–226°.

Analysis Calcd. for $C_{21}H_{22}F_6N_2O$: C, 58.34; H, 5.13; N, 6.48; F, 26.35. Found: C, 58.09; H, 5.06; N, 6.45; F, 26.22.

EXAMPLE 12

Preparation of epimeric 5(R)-ethyl-4(S)-quinuclidine-2ξ-carboxaldehydes

A. A solution containing 1.14 g. of 1,1-dichloro-3-[3(R)-ethyl-4(S)-piperidinyl]-propan-2(S)-ol hydrochloride in 20 ml. of water was combined with 450 ml. of benzene. The stirred mixture was cooled in an ice bath and 7.4 ml. of a 1.68N potassium hydroxide solution was added slowly. Stirring at room temperature was continued under an atmosphere of nitrogen for 20 hours. The aqueous layer was separated and extracted with benzene. The combined organic layer was dried over sodium sulfate and evaporated under reduced pressure at 30°. The residue on distillation in a Kugelrohr-distillation apparatus at 80° and 0.1 mm. mercury afforded 283 mg. (40%) of liquid epimeric 5(R)-ethyl-4(S)-quinuclidine-2ξ-carboxaldehyde.

Analysis Calcd. for $C_{10}H_{17}NO$: C, 71.81; H, 10.25; N, 8.38. Found: C, 71.75; H, 9.97; N, 8.44.

B. Utilizing the procedure above, a mixture of 1.94 g. of 1,1-dichloro-3-[3(R)-ethyl-4(S)-piperidinyl]propan-2(S)-ol hydrochloride and 1,1-dichloro-3-[3(R)-ethyl-4(S)-piperidinyl]propan-2(R)-ol hydrochloride gave after distillation at 80° and 0.3 mm. mercury, 538 mg. of epimeric 5(R)-ethyl-4(S)-quinuclidine-2ξ-carboxaldehydes $[\alpha]^{25}$ D = ±102.61° (c 1.168, methanol).

EXAMPLE 13

Preparation of epimeric 5(S)-ethyl-4(R)-quinuclidine-2ξ-carboxaldehydes

A solution containing 1.34 g. of 1,1-dichloro-3-[3(S)-ethyl-4(R)-piperidinyl]propan-2(S)-ol hydrochloride in 10 ml. of water was combined with 150 ml. of benzene. The stirred mixture was cooled in an ice-bath and 8.7 ml. of a 1.68N potassium hydroxide solution was added slowly. Stirring at room temperature was continued under an atmosphere of nitrogen for 20 hours. The aqueous layer was separated and extracted with benzene. The combined organic layer was dried over sodium sulfate and evaporated under reduced pressure at 30°. The residue on distillation afforded 500 mg. of liquid epimeric 5(S)-ethyl-4(R)-quinuclidine-2ξ-carboxaldehydes, b.p. 90° at 0.1 mm. mercury $[\alpha]^{25}$ D −85.56° (c 1.0682, methanol).

Analysis Calcd. for $C_{10}H_{17}NO$: C, 71.81; H, 10.25; N, 8.38. Found: C, 71.55; H, 10.29; N, 8.65.

EXAMPLE 14

Preparation of racemic 5′-chloro-2′-trifluoromethyldihydrocinchonidine and racemic 5′-chloro-2′-trifluoromethyldihydrocinchonine To 500 ml. of anhydrous ether was added 69.0 ml. of a 2.04 M solution of butyllithium in hexane. The resulting solution was cooled to −70° and with stirring 43.4 g. of 4-bromo-5-chloro-2-trifluoromethylquinoline dissolved in 100 ml. of anhydrous tetrahydrofuran was added under an atmosphere of nitrogen at such a rate as to maintain a temperature of −70°. Stirring of the solution containing the 5-chloro-2-trifluoromethyl-4-quinolyllithium was continued at this temperature for one hour followed by the dropwise addition of 25.9 g. of racemic 4,5-erythro-5-ethylquinuclidine-2ξ-carboxaldehyde dissolved in 100 ml. of anhydrous ether. The reaction mixture was stirred at −70° overnight, hydrolyzed with water and allowed to warm to room temperature. The ethereal solution was washed twice with water and the washings were backwashed with ether. The combined organic extract was dried over sodium sulfate and evaporated to dryness to yield 67.3 g. of a semi-solid residue. The crude material was treated with chloroform and the solid was collected by filtration to give 12 g. of crude racemic 5′-chloro-2′-trifluoromethyldihydrocinchonine as a white powder, m.p. 170°–178°. The mother liquor was placed on a silica gel column (2 kg. of silica gel Merck 60, i.d. of column 65 mm) and eluted with chloroform-acetone-triethylamine (5:4:1, solvent A). Fractions of 200 ml. were collected and the progress of the chemotherapy was monitored by thin layer chromatography on silica gel with solvent A as the liquid phase. The combined fractions were evaporated to dryness and the residue was dissolved in dichloromethane. The organic solution was washed with water, the aqueous layer was backwashed with dichloromethane, and the combined organic solution was dried over sodium sulfate and evaporated under reduced pressure. After 3.4 L. of forerun, the next 3.6 L. yielded 21.9 g. of a mixture of compounds. This was followed by 8.2 g. of crude racemic 5′-chloro-2′-trifluoromethyldihydrocinchonine eluted with 6 L. of solvent. Crystallization of the mixture from ether yielded 3.8 g. of racemic 5′-chloro-2′-trifluoromethyldihydrocinchonine, mp 182°–183° and 3.8 g. of racemic 5′-chloro-2′-trifluoromethyldihydrocinchonidine, mp 170°–172°. The mother liquor was chromatographed again on silica gel (500 g. of silica gel Merck 60) with chloroform-acetone-triethylamine (6:3:1) as the solvent. This chromatography gave additional 4 g. of the dihydrocinchonidine derivative, mp 160°–170° after crystallization from ether. Crude dihydrocinchonidine fractions were combined and recrystallized from ether to give 4.2 g. of analytical pure racemic 5′-chloro-2′-trifluoromethyldihydrocinchonidine, mp 175°–176° after drying at 100° for 20 hours under reduced pressure.

Analysis Calcd. for $C_{20}H_{22}ClF_3N_2O$ (398.87): C, 60.22; H, 5.56; N, 7.02; F, 14.29. Found: C, 60.39; H, 5.81; N, 7.03; F, 14.46.

Recrystallization of the combined crude dihydrocinchonine fractions from chloroform afforded 8.6 g. of analytically pure racemic 5′-chloro-2′-trifluoromethyldihydrocinchonine as a white powder, mp 192°–193° (dec.) after drying for 48 hours at 100° under reduced pressure.

Analysis Calcd. for $C_{20}H_{22}ClF_3N_2O$ (398.87): C, 60.22; H, 5.56; N, 7.02; F, 14.29. Found: C, 60.21; H, 5.72; N, 7.00; F, 14.38.

EXAMPLE 15

Preparation of the enantiomer of 2′,8′-bis(trifluoromethyl)-dihydrocinchonidine and the enantiomer of 2′,8′-bis(trifluoromethyl)-dihydrocinchonine To 150 ml. of anhydrous ether was added 27.5 ml. of a 1.6 M solution of butyllithium in hexane. This solution was combined at −70° under nitrogen with a solution of 15.5 g. of 2,8-bis(trifluoromethyl)-4-bromoquinoline in 150 ml. of anhydrous ether at such a rate as to maintain the low temperature. After completion of the addition, stirring of the mixture containing 2,8-bis(trifluoromethyl)-4-quinolyllithium was continued for another 30 minutes. Then, 7.1 g. of epimeric 5(S)-ethyl-4(R)-quinuclidine-2ξ-carboxaldehydes dissolved in 100 ml. of anhydrous ether were added. After stirring overnight at −70°, the reaction mixture is quenched with water and diluted with 300 ml. of ether. The ethereal solution was washed with water, dried over sodium sulfate and evaporated under reduced pressure. The residue (19.6 g.) was chromatographed on 2 kg. of silica gel (column i.d. 60 mm) with chloroform-acetone-triethylamine (5:4:1) as the solvent. Fractions of 150 ml. were collected. The progress of the chromatography was monitored by thin layer chromatography on silica gel with the same solvent. Combined fractions were evaporated and the residue was dissolved in dichloromethane. The organic solution was washed with water, the aqueous layer was backwashed with dichloromethane, and the combined organic solution was dried over sodium sulfate and evaporated under reduced pressure. After a forerun of 4 L. containing mostly unreacted starting materials, fractions 27–45 yielded 8.4g. of a mixture of the enantiomers of 2′,8′-bis(trifluoromethyl)-9-epi-dihydrocinchonidine and 2′,8′-bis(trifluoromethyl)-9-epi-dihydrocinchonine. Fractions 133–205 after workup yielded 4.2 g. of an oil which crystallized on standing and after two recrystallizations from ether afforded the analytically pure enantiomer of 2′,8′-bis(trifluoromethyl)dihydrocinchonine, mp 205°–206° after drying at 100° overnight under reduced pressure; $[\alpha]_D^{25}$ −122.17° (c 1.1157, methanol).

Analysis Calcd. for $C_{21}H_{22}F_6N_2O$ (432.36): C, 58.34; H, 5.13; N, 6.48; F, 26.35.
Found: C, 58.32; H, 5.06; N, 6.53; F, 26.24.

Continuation of the chromatography with the solvent system changed to chloroform-methanol-triethylamine (7:2:1) resulted in the isolation of 2.8 g. of a yellow solid from fractions 216-260. Two recrystalllizations of this material from ether yielded the analytically pure enantiomer of 2′,8′-bis(trifluoromethyl)-dihydrocinchonidine, mp 229°–230° after drying at 100° overnight under reduced pressure; $[\alpha]_D^{25}$ +57.06° (c 1.020, methanol).

Analysis Calcd. for $C_{21}H_{22}F_6H_2O$ (432.36): C, 58.34; H, 5.13; N, 6.48; F, 26.35. Found: C, 58.03; H, 4.89; N, 6.39; F, 26.49.

EXAMPLE 16

Preparation of 2′,8′-bis(trifluoromethyl)dihydrocinchonidine and 2′,8′-bis-(trifluoromethyl)dihydrocinchonine Sixty-five milliliters of a 1.6M solution of n-butyllithium in hexane dissolved in 250 ml. of anhydrous ether and 35.7 g. of 2,8-bis(trifluoromethyl)-4-bromoquinoline dissolved in 150 ml. of anhydrous ether were combined with stirring under nitrogen at such a rate as to maintain a temperature of −70°. After completion of the addition, stirring of the mixture containing 2,8-bis(trifluoromethyl)-4-quinolyllithium was continued for another 30 minutes which was then followed by the addition of 17 g. of epimeric 5(R)-ethyl-4(S)-quinuclidine-2ξ-carboxaldehydes dissolved in 150 ml. of anhydrous ether. The reaction mixture was stirred overnight at −70° and then quenched with water and diluted with 500 ml. of ether. After warming to room temperature, the ethereal solution was washed with water, dried over sodium sulfate and evaporated under reduced pressure. The residue (52.3 g.) was chromatographed on 2 kg. of silica gel (Merck 60, i.d. of column 60 mm) with chloroform-acetone-triethylamine (5:4:1) as the solvent. Fractions of 150 ml. were collected. The progress of the chromatography was monitored by thin layer chromatography on silica gel with the same solvent. Combined fractions were evaporated and the residue was dissolved in dichloromethane. The organic solution was washed with water, the aqueous layer was backwashed with dichloromethane, and the combined organic solution was dried over sodium sulfate and evaporated under reduced pressure.

After an empty forerun of 2.1 L., the next 7 fractions gave 8.3 g. of unreacted quinoline followed in the next 17 fractions by 22.3 g. of an oil consisting mainlu of unreacted aldehyde, 2′,8′-bis(trifluoromethyl)-9-epi-dihydrocinchonidine and 2′,8′-bis(trifluoromethyl)-9-epi-dihydrocinchonine. Fractions 128–202 afforded 14.3 g. of a white solid which after two recrystallizations from ether petroleum ether (30°–60°) gave analytically pure 2′,8′-bis(trifluoromethyl)-dihydrocinchonine, mp 205°–206° after drying at 100° overnight under reduced pressure; $[\alpha]_D^{25}$ + 124.38° (c 1.008, methanol).

Analysis Calcd. for $C_{21}H_{22}F_6N_2O$ (432.36): C, 58.34; H, 5.13; N, 6.48; F, 26.35. Found: C, 58.15; H, 5.21; N, 6.47; F, 26.43.

A mixture (1.1 g.) of 2′,8′-bis(trifluoromethyl)dihydrocinchonine and 2′,8′-bis(trifluoromethyl)dihydrocinchonidine was obtained from fractions 203–219.

After changing the solvent system after fraction 210 to chloroform-methanol-triethylamine (7:2:1) fractions 220–280 gave 5.3 g. of a white solid. Two recrystallizations from ether-petroleum ether (30-60°) yielded analytically pure 2′,8′-bis(trifluoromethyl)-dihydrocinchonidine in the form of white crystals, mp 229-230° after drying at 100° overnight under reduced pressure; $[\alpha]_D^{25}$ −57.06° (c 1.076, methanol).

Analysis Calcd. for $C_{21}H_{22}F_6N_2O$ (432.36): C, 58.34; H, 5.13; N, 6.48; F, 26.35. Found: C, 58.16; H, 5.20; N, 6.46; F, 26.27.

EXAMPLE 17

Preparation of epimeric 5(R)-vinyl-4(S)-quinuclidine-2ξ-carboxaldehydes

A solution containing 2.36 g. of a mixture of 1,1-dichloro-3-[3(R)-vinyl-4(S)-piperidinyl]propan-2(S)-ol hydrochloride and 1,1-dichloro-3-[3(R)-vinyl-4(S)-piperidinyl]propan-2(R)-ol hydrochloride in 35 ml. of water was combined with 850 ml. of benzene. The stirred mixture was cooled in an ice bath and 15.4 ml. of 1.68N potassium hydroxide solution was added slowly under a nitrogen atmosphere. Stirring at room temperature was continued for 16 hours. The aqueous layer was separated and extracted with benzene. The combined organic layer was washed with water, dried over sodium sulfate and evaporated under reduced pressure at 30°. The residue on distillation afforded 767 mg. of liquid epimeric 5(R)-vinyl-4(S)-quinuclidine-2ξ-carboxaldehydes, b.p. 60° at 0.05 mm. mercury $[\alpha]^{25}$ D +154.85° (c 0.8957, chloroform).

EXAMPLE 18

Preparation of 2′,8′-bis(trifluoromethyl)cinchonidine and 2′,8′-bis(trifluoromethyl)cinchonine To 150 ml. of anhydrous ether was added 17.6 ml. of a 2.04 M solution of n-butyllithium in hexane. The resulting solution was cooled to −70° and with stirring, 12.7 g. of 2,8-bis(trifluoromethyl)-4-bromoquinoline dissolved in 150 ml. of anhydrous ether was added under an atmosphere of nitrogen at such a rate as to maintain a temperature of −70°. Stirring of the solution containing the 2,8-bis(trifluoromethyl)-4-quinolyllithium was continued at this temperature for 30 minutes followed by the dropwise addition of 5.6 g. of epimeric 5(R)-vinyl-4(S)-quinuclidine-2ξ-carboxaldehydes dissolved in 50 ml. of anhydrous ether. The reaction mixture was stirred at −70° overnight, hydrolyzed with water and allowed to warm to room temperature. The ethereal solution was washed twice with water, dried over sodium sulfate and evaporated to dryness to yield 17.6 g. of crude material. This residue was chromatographed on 2 kg. of silica gel (Merck 60) with chloroform-acetone-triethylamine (5:4:1) as the solvent. Fractions of 150 ml. were collected. The progress of the chromatography was monitored by thin layer chromatography on silica gel with the same solvent. Combined fractions were evaporated and the residue was dissolved in dichloromethane. The organic solution was washed with water, the aqueous layer was backwashed with dichloromethane, and the combined organic solution was dried over sodium sulfate, and evaporated under reduced pressure. After a forerun of 2.7 L. containing mostly unreacted starting materials, the next 1.8 L. eluted 6.8 g. of a crude mixture of 2′,8′-bis(trifluoromethyl)-9-epi-cinchonine and 2′,8′-bis(trifluoromethyl)-9-epi-cinchonidine. Fractions 73–120 after workup yielded 1.7 g. of a yellow solid. Two recrystallizations from ether-petroleum ether (30°–60°) afforded analytically pure 2′,8′-bis(trifluoromethyl)-cinchonine, mp 199°–200° after drying at 100° overnight under reduced pressure; $[\alpha]_D^{25}$ +136.19° (c 1.1308; methanol).

Analysis Calcd. for $C_{21}H_{20}F_6N_2O$ (430.39): C, 58,61; H, 4.68; N, 6.51; F, 26.48. Found: C, 58.73; H, 4.87; N, 6.55; F, 26.41.

Continuation of the chromatography with the solvent system changed to chloroform-methanol-triethylamine (7:2:1) resulted in the isolation of 2.1 g. of white solid fractions 121–175. Two recrystallizations from ether afforded analytically pure 2′,8′-bis(trifluoromethyl)-cinchonidine, mp 225–226° after drying for 20 hours at 100° under reduced pressure; $[\alpha]_D^{25}$ −67.79° (c, 1.1137, methanol).

Analysis Calcd. for $C_{21}H_{20}F_6N_2O$ (430.39): C, 58.61; H, 4.68; N, 6.51; F, 26.48. Found: C, 58.73; H, 4.84; N, 6.44; F, 26.61.

In a manner analogous to that described in this example, the following compounds can be prepared:

2′,7′-bis(trifluoromethyl)cinchonidine;
2′,7′-bis(trifluoromethyl)cinchonine;
5′-chloro-2′-trifluoromethylcinchonidine;
5′-chloro-2′-trifluoromethylcinchonine;
7′-chloro-2′-trifluoromethylcinchonidine;
7′-chloro-2′-trifluoromethylcinchonine;
8′-chloro-2′-trifluoromethylcinchonidine; and
8′-chloro-2′-trifluoromethylcinchonine.

EXAMPLE 19

Preparation of racemic ethyl 4,5-erythro-5-ethyl-quinuclidine-2 ξ-carboxylate

To a solution of 8.3 g. of isomeric erythro-1,1-dichloro-3-(3-ethyl-4-piperidinyl)propan-2 ξ-ol hydrochlorides in 600 ml. of methanol cooled to 0° was added dropwise with stirring a solution of 5.04 g. of potassium hydroxide in 23.4 ml. of methanol. After the addition was completed, the temperature of the mixture was allowed to rise to room temperature and stirring was continued overnight. Insoluble material was removed by filtration and the solution was added to a mixture of 11.7 g. of silver nitrate and 4.8 g. of sodium hydroxide in 200 ml. of water. The reaction mixture after stirring for 3 hours at room temperature, was filtered through Celite-Filter Aid and the filtrate was saturated with hydrogen sulfide. The precipitate was removed by filtration through Celite-Filter Aid and the filtrate was evaporated to dryness. Complete dryness was ensured by the addition of an ethanol-benzene solvent mixture to the residue followed by removal of the solvents under reduced pressure. This procedure was repeated three times. The residue was treated with 500 ml. of ethanol, and the mixture was refluxed for 3 hours. After filtering through Celite-Filter Aid, the filtrate was saturated with anhydrous hydrogen chloride and refluxed overnight. The precipitate was removed by filtration, and the filtrate was evaporated to dryness. The yellow oil obtained was treated with 300 ml. of a saturated aqueous solution of sodium carbonate and extracted five times with ether. The combined ether extract was dried over sodium sulfate and evaporated to dryness under reduced pressure. The residue was distilled in a short path distillation apparatus at 70°–75° (oil bath temperature) under a pressure of 0.3 mm. of mercury to give 3.81 g. (60%) of liquid racemic ethyl 4,5-erythro-5-ethylquinuclidine-2 ξ-carboxylate. For analytical purposes, a sample was redistilled at 101° and 0.5 mm. mercury.

Analysis Calcd. for $C_{12}H_{21}NO_2$: C, 68.21; H, 10.02; N, 6.63. Found: C, 68.19; H, 9.84; N, 6.88.

Gas chromatography showed the material to consist of two isomers in a 1:1 ratio. A separation of the two isomers was achieved by preparative gas chromatography.

EXAMPLE 20

Preparation of racemic 2',8'-bis(trifluoromethyl)-dihydrocinchonidinone and racemic 2',8'-bis(trifluoromethyl)-dihydrocinchoninone A solution of 18.1 ml. of n-butyllithium (1.6 M in hexane) in 150 ml. of anhydrous ether was cooled to −70°. With stirring and under an atmosphere of nitrogen, 10.0 g. of 2,8-bis(trifluoromethyl)-4-bromoquinoline dissolved in 100 ml. of anhydrous ether was added over a period of 30 minutes. Subsequently, a solution of 6.15 g. of racemic ethyl 4,5-erythro-5-ethylquinuclidine-2ξ-carboxylate in 100 ml. of anhydrous ether was added slowly to the mixture containing the 2,8-bis(trifluoromethyl)-4-quinolyllithium. After the addition was completed, stirring was continued for 3 hours at −70°. The reaction was then quenched by the addition of water and allowed to warm up to room temperature. The organic solution was washed with water, dried over sodium sulfate and evaporated to dryness under reduced pressure to yield 16.1 g. of a mixture containing racemic 2',8'-bis(trifluoromethyl)-dihydrocinchonidinone and racemic 2',8'-bis(trifluoromethyl)-dihydrocinchoninone. This material was purified by chromatography on silica gel with benzene-ethyl acetate (1:1) as the solvent. The progress of the chromatography was monitored by thin layer chromatography on silica gel with the same solvent mixture. Fractions containing the desired material were combined and evaporated to dryness. The residue was treated with ethanolic hydrogen chloride and the resulting solid was recrystallized first from benzene-ether and subsequently from acetone-ether to give an epimeric mixture of racemic 2',8'-bis(trifluoromethyl)-dihydrocinchonidinone hydrochloride and racemic 2',8'-bis(trifluoromethyl)-dihydrocinchoninone hydrochloride as white crystals, mp 245–247°C. after drying at 100° for 20 hours under reduced pressure.

Analysis Calcd. for $C_{21}H_{20}F_6N_2O \cdot 0.5H_2O \cdot HCl$ (475.86): C, 53.01; H, 4.66; N, 5.89; F, 23.95. Found: C, 53.03; H, 4.41; N, 5.92; F, 23.42.

EXAMPLE 21

Preparation of racemic 2',8'-bis(trifluoromethyl)dihydrocinchonidine and racemic 2',8'-bis(trifluoromethyl)dihydrocinchonine A mixture of 11.0 g. of racemic 2',8'-bis(trifluoromethyl)dihydrocinchonidinone and racemic 2',8'-bis(trifluoromethyl)dihydrocinchoninone was dissolved in 100 ml. of anhydrous toluene and to the ice-cold solution was added over a period of 1 hour, 16.5 ml. of a 1.5 M solution of diisobutylaluminum hydride in toluene under an atmosphere of dry nitrogen. The reaction mixture was stirred for 1 hour at room temperature and then quenched by the addition of 10 ml. of water-methanol (1:1). The precipitate was collected by filtration through Celite filter-aid. The clear solution was washed with water, dried over sodium sulfate and evaporated to dryness under reduced pressure. The crude product (11 g.) was purified by column chromatography on silica gel (300 g., Merck 60). After an initial empty forerun of 1.4 L. (solvent: benzene) the solvent was changed to benzene-methanol (1:1) and fractions of 200 ml. were collected. Fractions 5–13 were combined and on evaporation yielded 2.2 g. of an oil. Crystallization from ether-benzene afforded 1.8 g. of a mixture of racemic 2',8'-bis(trifluoromethyl)-dihydrocinchonidine and racemic 2',8'-bis(trifluoromethyl)dihydrocinchonine. Chromatography on silica gel with chloroform-acetone-triethylamine (5:4:1) as the solvent gave racemic 2',8'-bis(trifluoromethyl)dihydrocinchonidine, mp 225°–226° after recrystallization from methanol, and racemic 2',8'-bis(trifluoromethyl)-dihydrocinchonine, mp 213°–215° after recrystallization from chloroform-ether.

In a manner analogous to that described in this example, the following compounds can be prepared:

rac. 2',7'-bis(trifluoromethyl)-dihydrocinchonidine: mp 221°–222°;
rac. 2',7'-bis(trifluoromethyl)-dihydrocinchonine: mp 201°–203°;
rac. 8'-chloro-2'-trifluoromethyl-dihydrocinchonidine: mp 234°–236°;
rac. 8'-chloro-2'-trifluoromethyl-dihydrocinchonine: mp 194°–196°;
rac. 7'-chloro-2'-trifluoromethyl-dihydrocinchonidine: mp 178°–180°;
rac. 7'-chloro-2'-trifluoromethyl-dihydrocinchonine: mp 203°–205°;
rac. 5'-chloro-2'-trifluoromethyldihydrocinchonidine: mp 175°–176°;
rac. 5'-chloro-2'-trifluoromethyldihydrocinchonine: mp 193°;
rac. 2',8'-bis(trifluoromethyl)-9-epi-dihydrocinchonidine: mp 149°–150°;
rac. 2',8'-bis(trifluoromethyl)-9-epi-dihydrocinchonine: mp 166°–168°;
enantiomer of 2',8'-bis(trifluoromethyl)-dihydrocinchonidine: mp 229°–230°;
enantiomer of 2',8'-bis(trifluoromethyl)-dihydrocinchonine: mp 205°–206°;
2',8'-bis(trifluoromethyl)-dihydrocinchonidine: mp 229°–230°;
2',8'-bis(trifluoromethyl)-dihydrocinchonine: mp 205°–206°;
2',8'-bis(trifluoromethyl)-cinchonidine: mp 225°–226°; and
2',8'-bis(trifluoromethyl)-cinchonine: mp 199°–200°.

EXAMPLE 22

Capsule Formulation

| | Per Capsule |
|---|---|
| Racemic 2',8'-bis(trifluoromethyl)-dihydrocinchonine | 50 mg. |

23

-continued

Capsule Formulation

| | Per Capsule |
|---|---|
| Corn Starch, U.S.P. | 150 mg. |
| Talc, U.S.P. | 10 mg. |
| Total Weight | 210 mg. |

Procedure

The racemic 2′,8′-bis(trifluoromethyl)dihydrocinchonine is mixed with corn starch in a suitable mixer. The mixture is further blended by passing through a Fitzpatrick Comminuting Machine with a No. 1A screen with knives forward. The blended powder is returned to the mixer, the talc added and blended thoroughly. The mixture is then filled into No. 4 hard shell gelatin capsules on a capsulating machine.

EXAMPLE 23

Tablet Formulation

| | Per Tablet |
|---|---|
| Racemic 2′,8′-bis(trifluoromethyl)-dihydrocinchonine | 25.00 mg. |
| Dicalcium Phosphate Dihydrate, Unmilled | 175.00 mg. |
| Corn Starch | 24.00 mg. |
| Magnesium Stearate | 1.00 mg. |
| Total Weight | 225.00 mg. |

Procedure

The racemic 2′,8′-bis(trifluoromethyl)dihydrocinchonine and corn starch are mixed together and passed through a No. 00 screen in Model "J" Fitzmill with hammers forward. This premix is then mixed with dicalcium phosphate and one-half of the magnesium stearate, passed through a No. 1A screen in Model "J" Fitzmill with knives forward, and slugged. The slugs are passed through a No. 2A plate in a Model "D" Fitzmill at slow speed with knives forward, and the remaining magnesium stearate is added. The mixture is mixed and compressed.

EXAMPLE 24

Suppository Formulation

| | Per 1.3 Gm. Suppository |
|---|---|
| Racemic 2′,8′-bis(trifluoromethyl)-dihydrocinchonine | 0.025 gm. |
| Hydrogenated coconut oil | 1.230 gm. |
| Carnauba Wax | 0.045 gm. |

Procedure

The hydrogenated coconut oil and the carnauba wax are melted in a suitable size glass-lined container (stainless steel may also be used), mixed well and cooled to 45°C. The racemic 2′,8′-bis(trifluoromethyl)dihydrocinchonine which has been reduced to a fine powder with no lumps, is added and stirred until completely and uniformly dispersed. The mixture is poured into suppository molds to yield suppositories having an individual weight of 1.3 gms. The suppositories are cooled, removed from molds, and individually wrapped in wax paper for packaging. (Foil may also be used.)

We claim:

1. A compound of the formula

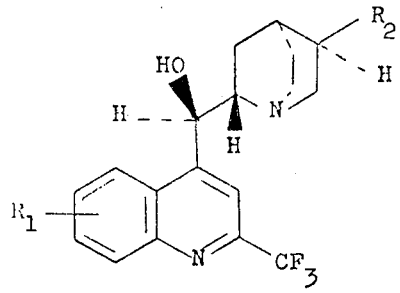

and

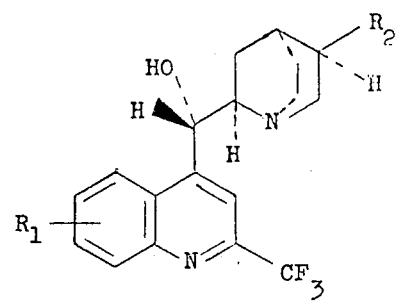

its enantiomer or racemate,
wherein $R_1$ is halogen or trifluoromethyl; and $R_2$ is ethyl or vinyl, or an addition salt thereof with a pharmaceutically acceptable acid.

2. A compound in accordance with claim 1, wherein $R_2$ is ethyl.

3. A compound in accordance with claim 1, wherein $R_2$ is vinyl.

4. The compound in accordance with claim 1, i.e., racemic 2,8-bis(trifluoromethyl)-α(R)-[5(R)-ethyl-4(S)-quinuclidin-2(S)-yl]-4-quinolinemethanol.

5. The compound in accordance with claim 1, i.e., 2,8-bis(trifluoromethyl)-α(S)-[5(S)-ethyl-4(R)-quinuclidin-2(R)-yl]-4-quinolinemethanol.

6. The compound in accordance with claim 1, i.e., racemic 2,8-bis(trifluoromethyl)-α(S)-[5(R)-ethyl-4(S)-quinuclidin-2(R)-yl]-4-quinolinemethanol.

7. The compound in accordance with claim 1, i.e., 2,8-bis(trifluoromethyl)-α(R)-[5(S)-ethyl-4(R)-quinuclidin-2(S)-yl]-4-quinolinemethanol.

8. The compound in accordance with claim 1, i.e., 2,8-bis(trifluoromethyl)-α(R)-[5(R)-vinyl-4(S)-quinuclidin-2-(S)-yl]-4-quinolinemethanol.

9. The compound in accordance with claim 1, i.e., 2,8-bis(trifluoromethyl)-α(S)-[5(R)-vinyl-4(S)-quinuclidin-2(R)-yl]-4-quinolinemethanol.

10. The compound in accordance with claim 1, i.e., racemic 2,7-bis(trifluoromethyl)-α(R)-[5(R)-ethyl-4(S)-quinuclidin-2(S)-yl]4-quinolinemethanol.

11. The compound in accordance with claim 1, i.e., racemic 2,7-bis(trifluoromethyl)-α(S)-[5(R)-ethyl-4(S)-quinuclidin-2(R)-yl]-4-quinolinemethanol.

12. The compound in accordance with claim 1, i.e., racemic 8-chloro-2-trifluoromethyl-α(R)-[5(R)-ethyl-4(S)-quinuclidin-2(S)-yl]-4-quinolinemethanol.

13. The compound in accordance with claim 1, i.e., racemic 8-chloro-2-trifluoromethyl-α(S)-[5(R)-ethyl- 4(S)-quinuclidin-2(R)-yl]-4-quinolinemethanol.

14. The compound in accordance with claim 1, i.e., racemic 7-chloro-2-trifluoromethyl-α(R)-[5(R)-ethyl-4(S)-quinuclidin-2(S)-yl]-4-quinolinemethanol.

15. The compound in accordance with claim 1, i.e., racemic 7-chloro-2-trifluoromethyl-α(S)-[5(R)-ethyl-4(S)-quinuclidin-2(R)-yl]-4-quinolinemethanol.

16. The compound in accordance with claim 1, i.e., racemic 5-chloro-2-trifluoromethyl-α(R)-[5(R)-ethyl-4(S)-quinuclidin-2(S)-yl]-4-quinolinemethanol.

17. The compound in accordance with claim 1, i.e., racemic 5-chloro-2-trifluoromethyl-α(S)-[5(R)-ethyl-4(S)-quinuclidin-2(R)-yl]-4-quinolinemethanol.

18. The compound in accordance with claim 1, i.e., 2,8-bis(trifluoromethyl)-α(R)-[5(R)-ethyl-4(S)-quinuclidin-2(S)-yl]-4-quinolinemethanol.

19. The compound in accordance with claim 1, i.e., 2,8-bis(trifluoromethyl)-α(S)-[5(R)-ethyl-4(S)-quinuclidin-2(R)-yl]-4-quinolinemethanol.

20. A compound of the formula

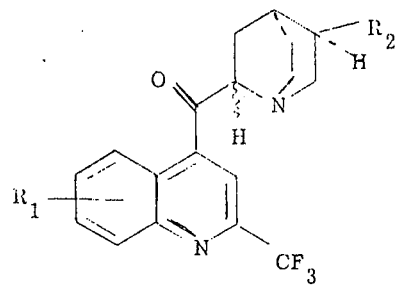

enantiomers and racemates thereof, wherein $R_1$ is halogen or trifluoromethyl; and $R_2$ is ethyl or vinyl and salts thereof with pharmaceutically acceptable acids.

21. A compound in accordance with claim 20, i.e., epimeric mixture of racemic 2,8-bis(trifluoromethyl)-4-[5(R)-ethyl-4(S)-quinuclidin-2 ξ-ylcarbonyl]quinolines.

* * * * *